United States Patent
Ryu (10) Patent No.: US 11,540,869 B2
(45) Date of Patent: Jan. 3, 2023

(54) HIGH FREQUENCY HYPERTHERMIA DEVICE AND HYPERTHERMIA METHOD USING THE SAME

(71) Applicant: HUREV Co., Ltd, Wonju-si (KR)

(72) Inventor: Kihong Ryu, Wonju-si (KR)

(73) Assignee: HUREV CO., LTD, Wonju-si (KR)

( * ) Notice: Subject to any disclaimer, the term of this patent is extended or adjusted under 35 U.S.C. 154(b) by 368 days.

(21) Appl. No.: 16/990,128

(22) Filed: Aug. 11, 2020

(65) Prior Publication Data
US 2022/0022936 A1    Jan. 27, 2022

(30) Foreign Application Priority Data
Jul. 24, 2020 (KR) .......................... 10-2020-0092305

(51) Int. Cl.
| | | |
|---|---|---|
| A61B 18/14 | (2006.01) | |
| A61B 18/12 | (2006.01) | |
| A61B 18/00 | (2006.01) | |

(52) U.S. Cl.
CPC .......... A61B 18/14 (2013.01); A61B 18/1206 (2013.01); *A61B 2018/0047* (2013.01);
(Continued)

(58) Field of Classification Search
CPC . A61B 18/1206; A61B 18/14; A61B 18/1402; A61B 2018/0016;
(Continued)

(56) References Cited

U.S. PATENT DOCUMENTS 5,454,809 A * 10/1995 Janssen .............. A61B 18/1206
606/41
6,023,638 A * 2/2000 Swanson .............. A61B 5/6855
606/41
(Continued)

FOREIGN PATENT DOCUMENTS

KR    10-2017-0068697 A    6/2017
KR    10-1833976 B1    3/2018
(Continued)

*Primary Examiner* — Michael F Peffley
(74) *Attorney, Agent, or Firm* — Bridgeway IP Law Group, PLLC; Sang Ho Lee; Hyun Woo Shin (57) ABSTRACT

Provided is a high frequency hyperthermia device which includes a main body (110) which includes a high frequency generator (114) which generates high frequency currents using drive power, a hand piece (120) which is connected to the main body (110) through a cable (140) and in which a handle (121) to be gripped by a user is disposed on an upper portion of the hand piece (120), and four or more contact electrodes (122), through which the high frequency currents being supplied are applied to skin (S) in contact with the contact electrodes (122) to generate deep heat in an internal body, are disposed on a lower surface of the hand piece (120), and an alternating switch (130) which is disposed between and connected to the high frequency generator (114) and the contact electrodes (122) in a circuit manner and which supplies the high frequency currents output from the high frequency generator (114) to the contact electrode (122), wherein the contact electrodes (122) are divided into pairs each having two contact electrodes (122), and the high frequency currents are alternately supplied to the pairs at a first speed.

12 Claims, 11 Drawing Sheets

(52) U.S. Cl.
CPC .............. *A61B 2018/00208* (2013.01); *A61B 2018/00291* (2013.01); *A61B 2018/00464* (2013.01); *A61B 2018/00922* (2013.01)

(58) Field of Classification Search
CPC .......... A61B 2018/00208; A61B 2018/00291; A61B 2018/00458; A61B 2018/00464; A61B 2018/0047; A61B 2018/0066; A61B 2018/0072; A61B 2018/00732; A61B 2018/00738; A61B 2018/00922; A61B 2018/00994; A61B 2018/124; A61N 2005/0644; A61N 2005/0651; A61N 5/0616; A61N 5/0624
See application file for complete search history.

(56) References Cited

U.S. PATENT DOCUMENTS

| | | | | |
|---|---|---|---|---|
| 6,638,277 | B2* | 10/2003 | Schaefer | A61B 18/1477 606/41 |
| 2008/0200861 | A1* | 8/2008 | Shalev | A61Q 9/04 604/20 |
| 2016/0121108 | A1 | 5/2016 | Kondo et al. | |

FOREIGN PATENT DOCUMENTS

| | | |
|---|---|---|
| WO | 02/03875 A1 | 1/2002 |
| WO | 2008/012827 A2 | 1/2008 |

* cited by examiner

HIGH FREQUENCY HYPERTHERMIA DEVICE AND HYPERTHERMIA METHOD USING THE SAME

CROSS-REFERENCE TO RELATED APPLICATION

This application claims priority to and the benefit of Korean Patent Application No. 10-2020-0092305, filed on Jul. 24, 2020, the disclosure of which is incorporated herein by reference in its entirety.

BACKGROUND

1. Field of the Invention

The present invention relates to a high frequency hyperthermia device and a hyperthermia method using the same, and more specifically, to a high frequency hyperthermia device which applies high frequency energy to the skin to generate deep heat inside the body or around the skin so that body treatment, such as skin tissue improvement, visceral fat melting, cancer cell necrosis, or the like, is performed and a hyperthermia method using the same.

2. Discussion of Related Art

Figure 1:
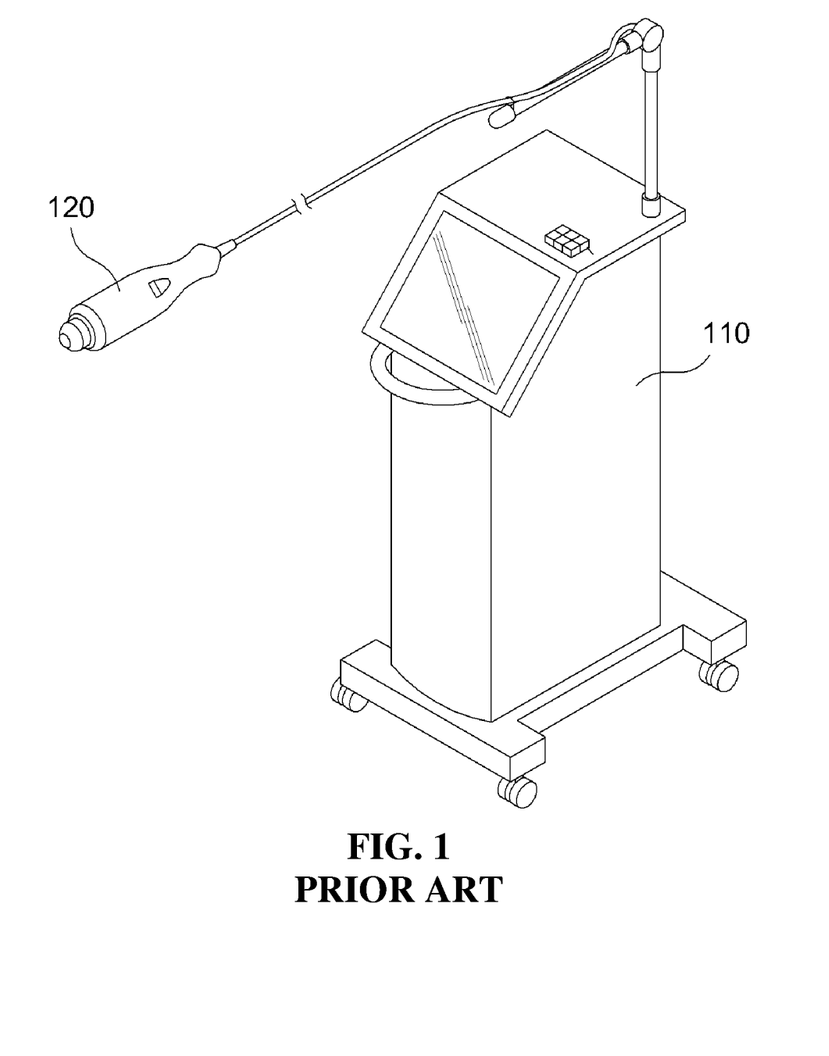
FIG. 1 is a perspective view illustrating a structure of a high frequency hyperthermia device according to a conventional technology.

In FIG. 1, components of a conventional high frequency hyperthermia treatment apparatus are illustrated. Referring to the drawing, the conventional high frequency hyperthermia device may mainly include a main body 110 and a hand piece 120, the main body 110 may receive external power and generate a high frequency current, and the high frequency current may be transmitted to the hand piece 120 through a cable and provided to the skin surface in the form of energy using a plurality of electrodes included in the hand piece 120.

However, in the conventional high frequency hyperthermia device, since the high frequency current having a fixed pole is applied to each of the electrodes of the hand piece 120, a region in which deep heat is generated in the inner body is small, heat performance is degraded, and thus there are problems in that a procedure time becomes longer and a treatment effect is insignificant.

In addition, in a case in which a procedure region is large, since the pole of the high frequency current applied to each of the electrodes is fixed, the procedure is performed by continuously moving the hand piece 120 and applying the high frequency current in a state in which the electrode is in contact with the skin, and thus fatigue is easily accumulated in a hand manipulating the hand piece. In addition, since a force applied to the electrode to press against the skin is not constant, a spark may occur between the electrode and the skin due to an unstable contact therebetween, and thus there are problems in that a patient may feel severe discomfort and fear, and the skin may also be burnt due to the spark in a severe case.

SUMMARY OF THE INVENTION

The present invention is directed to a high frequency hyperthermia device and a hyperthermia method which may generate deep heat in a short time by alternately applying high frequency currents to electrodes disposed on a lower surface of a hand piece to be spaced apart from each other at a first speed, may reduce a procedure time and improve a treatment effect by heating an entirety of a relatively large area, and may minimize discomfort, fear, and a burning possibility due to a spark by reducing a need to move the electrodes in contact with the skin.

According to an aspect of the present invention, there is provided a high frequency hyperthermia which includes a main body (110) including a high frequency generator (114) which generates high frequency currents using drive power, a hand piece (120) which is connected to the main body (110) through a cable (140) and in which a handle (121) to be gripped by a user is disposed on an upper portion of the hand piece (120), and four or more contact electrodes (122), through which high frequency currents being supplied are applied to skin (S) in contact with the contact electrodes (122) to generate deep heat in an internal body, are disposed on a lower surface of the hand piece (120), and an alternating switch (130) which is disposed between and connected to the high frequency generator (114) and the contact electrodes (122) in a circuit manner and which supplies the high frequency currents output from the high frequency generator (114) to the contact electrode (122), wherein the contact electrodes (122) are divided into pairs each having two contact electrodes (122), and the high frequency currents are alternately supplied to the pairs at the first speed.

In this case, the contact electrodes (122) may be disposed on a lower portion (125) of the hand piece (120) to be spaced apart from each other by a predetermined distance along a circumference around a center (C1) of the hand piece (120), and the alternating switch (130) may apply the high frequency current with a positive pole to one contact electrode (122) and the high frequency current with a negative pole to the other contact electrode (122) to alternately supply the high frequency currents to each of the pairs so as to generate the deep heat, wherein the contact electrodes (122) may be divided into the pairs such that two contact electrodes (122) opposite to each other with respect to the center (C1) form the pair.

In addition, the alternating switch (130), which is disposed in the hand piece (120), may include a rotation plate (131) disposed close to the contact electrodes (122) in the hand piece (120) to be rotatable about the center (C1), a positive pole electrode (132) which is connected to the high frequency generator (114) in a circuit manner, receives the high frequency current with the positive pole, is disposed at one side of the rotation plate (131), and comes into contact with one contact electrode (122) included in any one pair to apply the high frequency current with the positive pole to the one contact electrode (122), a negative pole electrode (133) which is connected to the high frequency generator (114) in a circuit manner, receives the high frequency current with the negative pole, is disposed at the other side of the rotation plate (131), and comes into contact with the other contact electrode (122) of the pair to apply the high frequency current with the negative pole to the other contact electrode (122), and a drive motor (134) which provides drive power required to rotate the rotation plate (131) and rotates the rotation plate (131) so that the positive pole electrode (132) and the negative pole electrode (133) sequentially and alternately come into contact with the contact electrodes (122).

In addition, the alternating switch (130), which is disposed in the main body (110), may include auxiliary electrodes (135) of which the number corresponds to the contact electrodes (122) and which are respectively connected to the contact electrodes (122) through the cable (140) and disposed to be spaced apart from each other by a predetermined distance along a circumference around a center (C2) of the alternating switch (130), a rotation plate (131) disposed close to the auxiliary electrodes (135) in the main body (110) to be rotatable about the center (C2), a positive pole electrode (132) which is connected to the high frequency generator (114) in a circuit manner, receives the high frequency current with the positive pole, is disposed at one side of the rotation plate (131), and comes into contact with one contact electrode (122) included in any one pair to apply the high frequency current with the positive pole to the one contact electrode (122), a negative pole electrode (133) which is connected to the high frequency generator (114) in a circuit manner, receives the high frequency current with the negative pole, is disposed at the other side of the rotation plate (131), and comes into contact with the other contact electrode (122) included in the pair to apply the high frequency current with the negative pole to the other contact electrode (122), and a drive motor (134) which provides drive power required to rotate the rotation plate (131) and rotates the rotation plate (131) such that the positive pole electrode (132) and the negative pole electrode (133) each sequentially come into contact with the contact electrodes (122).

In addition, the main body (110) may further include a suction driver (116) which provides a suction pressure, a suction pipe (123) communicating with a suction end of the suction driver (116) through the cable (140) is disposed in the hand piece (120), and a suction groove (124), which has a shape concavely recessed upward and of which one side communicates with the suction pipe (123) such that the skin (S) in contact with the lower portion (125) of the hand piece (120) is suctioned into the suction groove (124), is formed at a center of the lower portion (125) of the hand piece (120).

In addition, the high frequency hyperthermia device may further comprise one or more LED modules which are disposed on the lower surface of the hand piece (120) and from which light treatment is applied to skin (S).

In addition, the frequency of the high frequency generator (114) may be controlled to change the depth at which deep heat is generated. The first speed of the alternating switch (130) or the high frequency currents output from the high frequency generator (114) may be controlled to change the amplitude of deep heat.

Meanwhile, according to another aspect of the present invention, there is provided a hyperthermia method of generating deep heat in an internal body using a high frequency hyperthermia device (1) which includes a main body (110) including a high frequency generator (114) which generates high frequency currents using drive power, a hand piece (120) which is connected to the main body (110) through a cable (140) and in which a handle (121) to be gripped by a user is disposed on an upper portion of the hand piece (120), and four or more contact electrodes (122) through which high frequency currents being supplied are applied to skin (S) in contact with the contact electrodes (122) to generate deep heat in an internal body are disposed on a lower portion of the hand piece (120), and an alternating switch (130) which is disposed between and connected to the high frequency generator (114) and the contact electrodes (122) in a circuit manner, supplies the high frequency currents output from the high frequency generator (114) to the contact electrode (122), wherein the contact electrodes (122) are divided into pairs each having two contact electrodes (122), and the high frequency currents are alternately supplied to the pairs at the first speed, the method including bringing the electrodes into contact with the skin (S210), in which the handle (121) of the hand piece (120) is gripped and the contact electrodes (122) simultaneously come into contact with the skin (S) of a diseased area, generating high frequency (S230), in which the high frequency generator (114) generates the high frequency currents according to manipulation of a user input unit (111) of the main body (110), and alternately supplying the high frequency currents (S240), in which the alternating switch (130) operates to supply the high frequency currents output from the high frequency generator (114) to the contact electrodes (122) such that the high frequency currents are each alternately supplied to the pairs at the first speed to generate the deep heat in the skin (S) in contact with the contact electrodes (122).

In this case, the main body (110) may further include a suction driver (116) which provides a suction pressure, a suction pipe (123) communicating with a suction end of the suction driver (116) through the cable (140) may be disposed in the hand piece (120), a suction groove (124) which has a shape concavely recessed upward and of which one side communicates with the suction pipe (123) such that the skin (S) in contact with the lower portion (125) of the hand piece (120) is suctioned into the suction groove (124) may be formed in a central portion of the lower portion (125) of the hand piece (120), suctioning the skin (S220) may be further performed so that the suction driver (116) generates a set suction pressure and suctions the skin (S) in contact with the hand piece (120) into the suction groove (124) after the bringing of the electrodes into contact with the skin (S210), the alternately supplying of the high frequency currents (S240) may be performed to generate the deep heat in a region positioned below the skin (S) suctioned into the suction groove (124) after the suctioning of the skin (S220), and diffusing the deep heat (S250) for waiting for a predetermined time may be further performed such that the suction driver (116) stops the generating of the suction pressure to return the skin (S) suctioned into the suction groove (124) to an original position due to elasticity, the region at which the deep heat is generated is returned to an original position, and the deep heat is diffused therearound after the alternately supplying of the high frequency currents (S240).

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Hereinafter, exemplary embodiments of the present invention will be described with reference to the accompanying drawings. Moreover, terms and words used in this specification and claims should not be interpreted as limited to commonly used meanings or meanings in dictionaries and should be interpreted with meanings and concepts which are consistent with the technological scope of the invention based on the principle that the inventors have appropriately defined concepts of terms in order to describe the invention in the best way.

Therefore, since the embodiments described in this specification and configurations illustrated in the drawings are only exemplary embodiments and do not represent the overall technological scope of the invention, it is understood that the invention covers various equivalents, modifications, and substitutions at the time of filing of this application.

Figure 2:
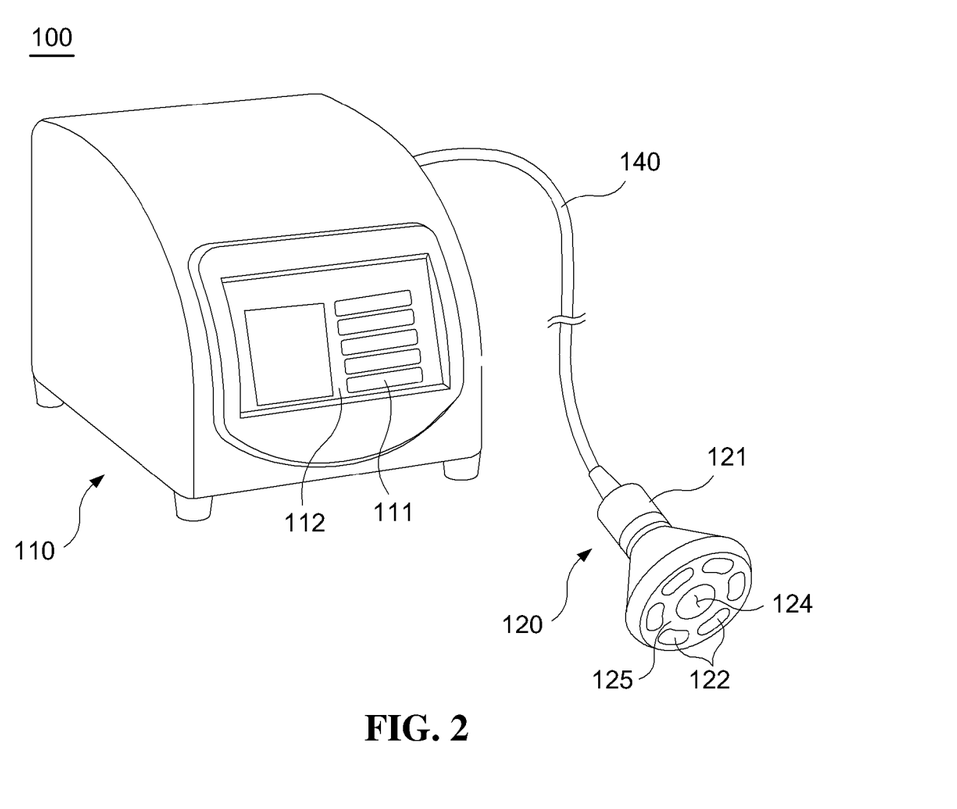
FIG. 2 is a perspective view illustrating a structure of a high frequency hyperthermia device according to an exemplary embodiment of the present invention.
Figure 3:
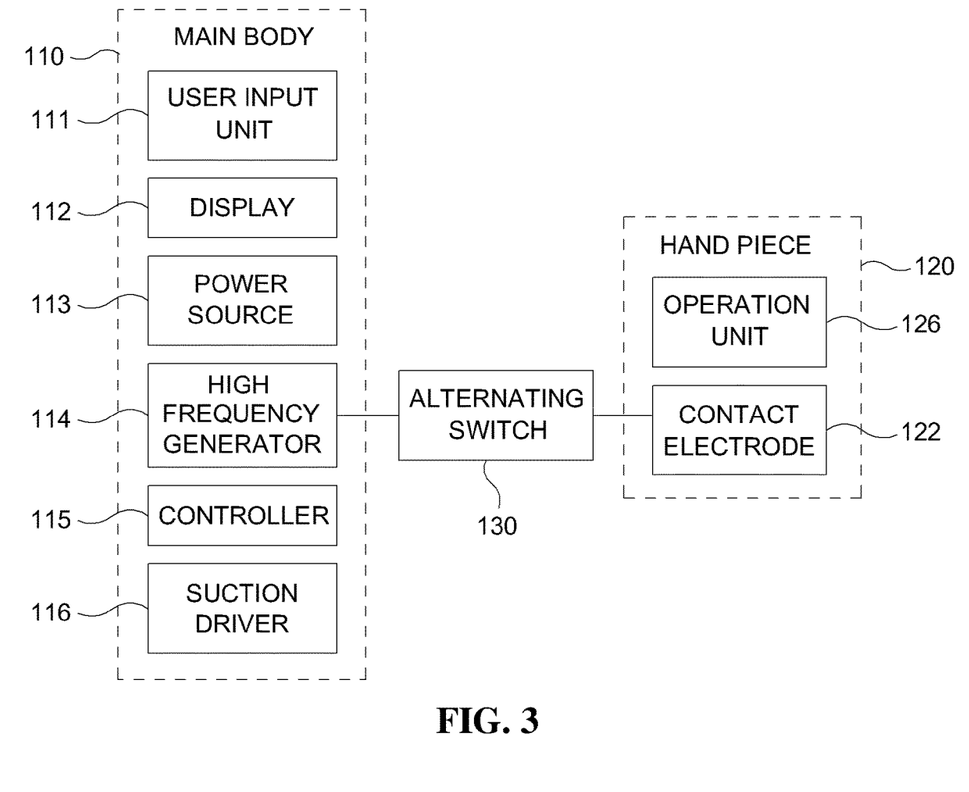
FIG. 3 is a block diagram illustrating a functional structure of the high frequency hyperthermia device according to the exemplary embodiment of the present invention.

First, a structure and a function of a high frequency hyperthermia device 100 according to an exemplary embodiment of the present invention will be described. The high frequency hyperthermia device 100 according to the exemplary embodiment of the present invention is a hyperthermia treatment apparatus capable of generating deep heat in a short time, heating an entirety of a relatively large area to significantly reduce a procedure time and improve a treatment effect, and reducing a need to move contact electrodes 122 in contact with the skin so that discomfort, fear, and a burning possibility due to spark may be minimized. The high frequency hyperthermia device 100 includes a main body 110, a hand piece 120, and an alternating switch 130 as illustrated in FIGS. 2 and 3.

The main body 110 incudes a high frequency generator 114, generates a high frequency current using supplied drive power, and transmits the generated high frequency current to the alternating switch 130. In this case, the main body 110 includes a user input unit 111 as illustrated in the drawings so that a user may manipulate an operation state and a set state of the high frequency hyperthermia device 100 and includes a display 112 so that various operation states and set states may be displayed using images, letters, or numbers.

In addition, a power source 113 which supplies drive power to the high frequency generator 114 may be formed as a conversion circuit which receives commercial power and generates the drive power converted to have required power characteristics (for example, DC 15 V, 120 Hz) and may also be formed in the form of a battery which receives and stores charging power, and supplies the charged drive power to the high frequency generator 114 as necessary, and the controller 115 is provided to control the high frequency hyperthermia device 100 to be operated by a program according to an input signal from the user input unit 111.

The hand piece 120 is a part used to be gripped and manipulated to adjust a position of the skin S to which a high frequency current is applied and is connected to the main body 110 through a cable 140, a handle 121 to be gripped by the user is provided on an upper portion of the hand piece 120, and four or more contact electrodes 122 which apply the received high frequency current to the skin S in contact therewith to generate deep heat in an internal body are disposed on a lower surface of the hand piece 120 to be spaced apart from each other.

Unlike a conventional high frequency hyperthermia device which applies high frequency currents of which poles are fixed to electrodes, the alternating switch 130, which is a switch for supplying alternating high frequency currents to the contact electrodes 122, is disposed between and connected to the high frequency generator 114 and the contact electrodes 122 in a circuit manner and supplies the high frequency currents output from the high frequency generator 114 to the contact electrodes 122, the contact electrodes 122 are divided into pairs of contact electrodes 122 and the pairs of the contact electrodes 122 alternately receive the high frequency currents, wherein the pair of contact electrodes 122 include two contact electrodes 122.

Figure 4:
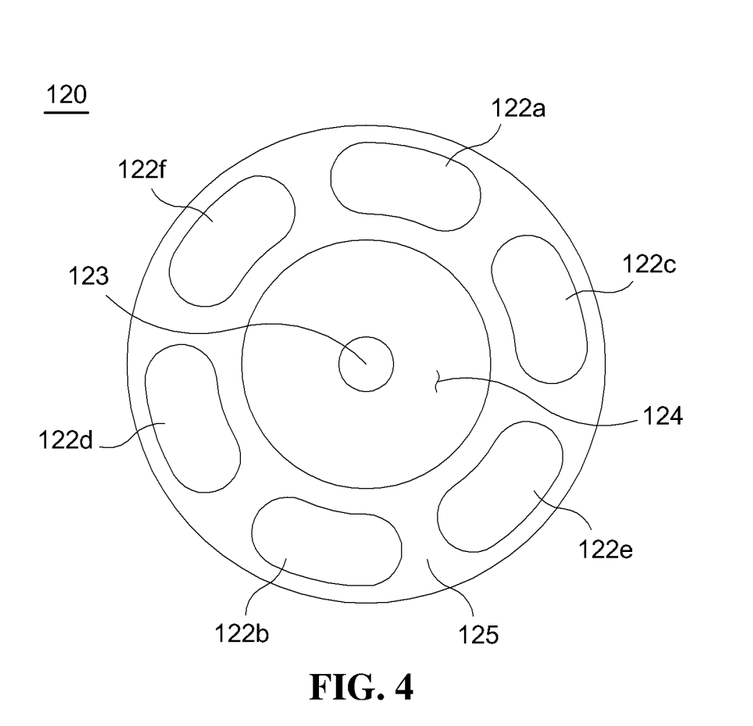
FIG. 4 is a captured image showing contact electrodes installed on a lower surface of a hand piece according to the exemplary embodiment of the present invention.

In this case, as illustrated in FIG. 4, the contact electrodes 122 may be disposed to be spaced apart from each other along a circumference thereof around a center C1 of a lower portion 125 of the hand piece 120, and thus, flows of the high frequency currents flowing in the body may be concentrated on a central portion by the pairs of contact electrodes 122 to decrease a deep heat generation time and significantly improve heat performance. For example, six contact electrodes 122 are divided into a pair including a contact electrode 122a in a 12 o'clock direction and a contact electrode 122b in a 6 o'clock direction, a pair including a contact electrode 122c in a 2 o'clock direction and a contact electrode 122d in an 8 o'clock direction, and a contact electrode 122e in a 4 o'clock direction and a contact electrode 122f in a 10 o'clock direction, and the high frequency current may be supplied to each of the pairs.

Figure 5:
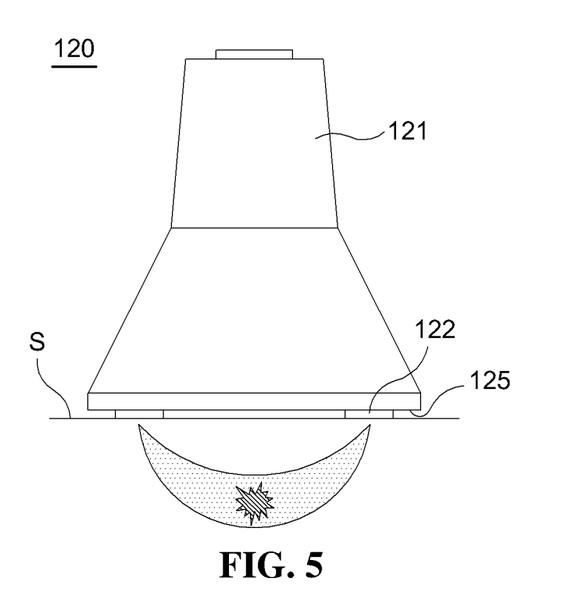
FIG. 5 is a side view illustrating an operation principle of generating deep heat in an internal body using the contact electrodes according to the exemplary embodiment of the present invention.

In addition, as illustrated in FIG. 5, when a high frequency current with a positive pole is applied to one contact electrode 122 of two contact electrodes 122 included in the pair, and a high frequency current with a negative pole is applied to another contact electrode 122, a current flows from a negative pole side to a positive pole side, and the current flows deeply to an internal body so that deep heat is generated.

Figure 6:
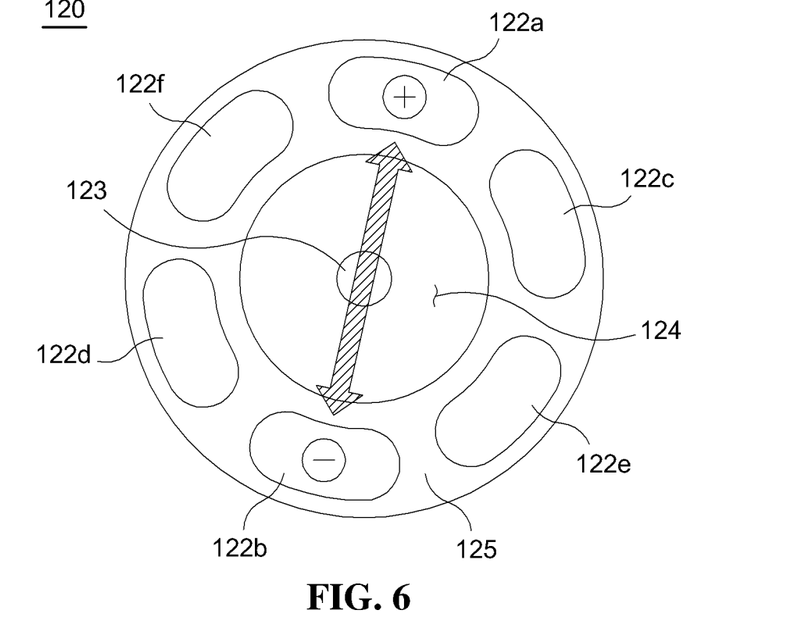
FIGS. 6 to 8 are images for describing an operation principle of alternately supplying high frequency currents to the contact electrodes according to the exemplary embodiment of the present invention.
Figure 7:
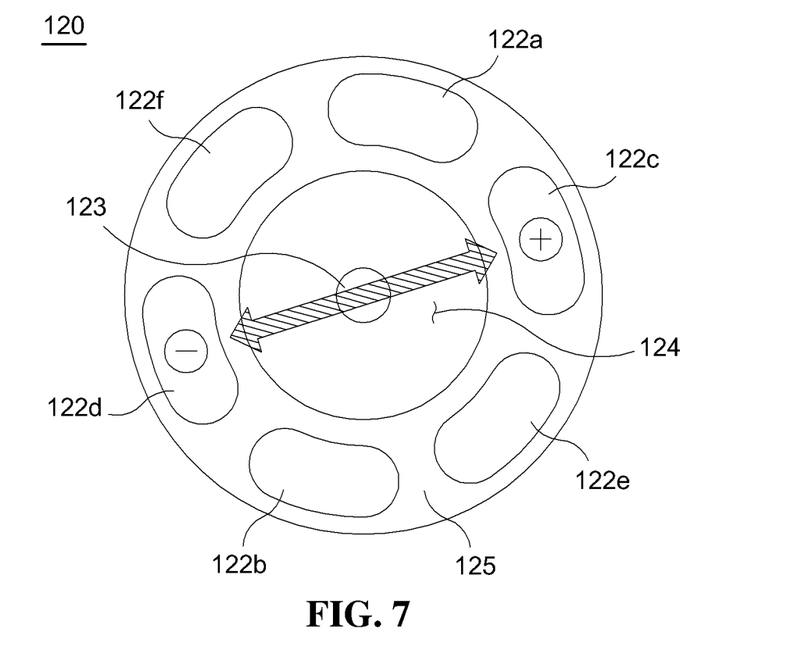
Figure 8:
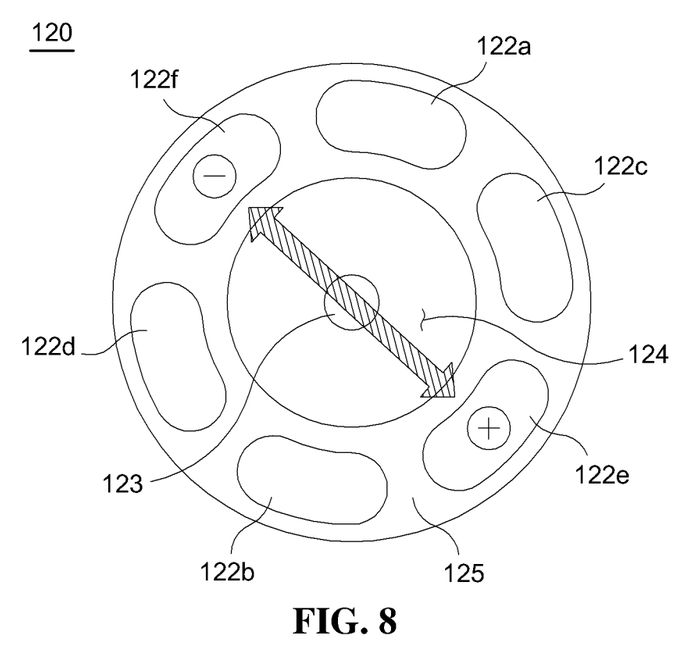

Accordingly, as illustrated in FIGS. 6 to 8, the contact electrodes 122 are divided such that two contact electrodes 122 opposite to each other with respect to the center C1 are formed in the pair, and the alternating switch 130 may apply the high frequency current with the positive pole to the contact electrode 122 included in the pair and apply the high frequency current with the negative pole to another contact electrode 122 to alternately supply the high frequency currents to the pairs to generate deep heat.

Figure 9:
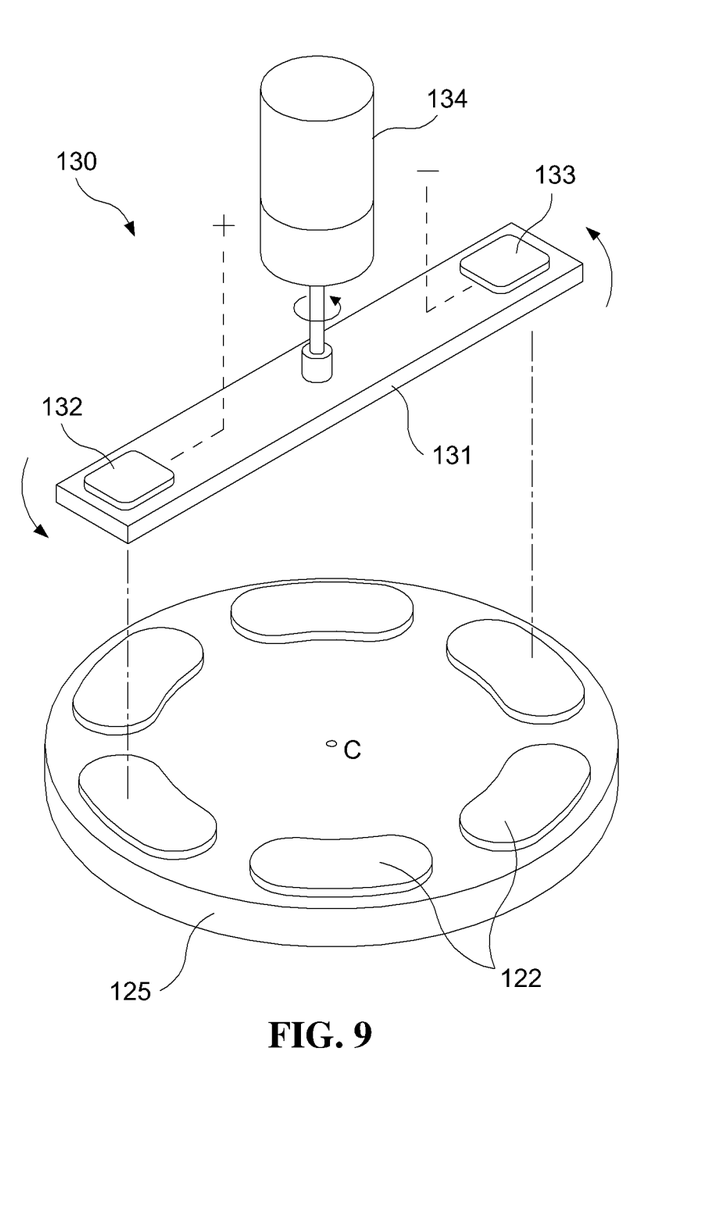
FIGS. 9 and 10 are a perspective view and a side view illustrating a structure in which an alternating switch is installed in the hand piece according to the exemplary embodiment of the present invention.
Figure 10:
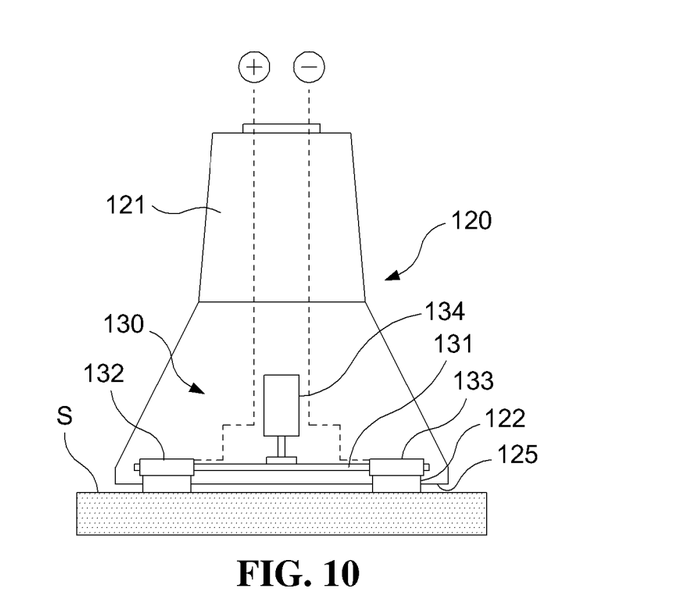

In addition, the alternating switch 130 may be installed in the hand piece 120 or the main body 110. First, as illustrated in FIGS. 9 and 10, in a case in which the alternating switch 130 is installed in the hand piece 120, the alternating switch 130 may include a rotation plate 131 disposed close to the contact electrodes 122 in the hand piece 120 to be rotatable about the center C1, a positive pole electrode 132 which is connected to the high frequency generator 114 in a circuit manner, receives a high frequency current with a positive pole, is disposed at one side of the rotation plate 131, and comes into contact with one contact electrode 122 included in any one pair to apply the high frequency current with the positive pole to the one contact electrode 122, a negative pole electrode 133 which is connected to the high frequency generator 114 in a circuit manner, receives a high frequency current with a negative pole, is disposed at the other side of the rotation plate 131, and comes into contact with the other contact electrode 122 of the pair to apply the high frequency current with the negative pole to the other contact electrode 122, and a drive motor 134 which provides drive power required to rotate the rotation plate 131 and rotates the rotation plate 131 so that the positive pole electrode 132 and the negative pole electrode 133 sequentially and alternately come into contact with the contact electrodes 122. Accordingly, the high frequency currents can be alternately applied using the simple structure and thus a manufacturing cost and a maintenance cost can be reduced.

In this case, sizes of the positive pole electrode 132 and the negative pole electrode 133 may be relatively greater than distances between the contact electrodes 122 installed on the lower portion 125 of the hand piece 120 to simultaneously come into contact with two adjacent contact electrodes 122 while rotating such that the high frequency currents applied to the skin S are not interrupted. Accordingly, a phenomenon in which a spark occurs on the skin S due to an unstable contact can be prevented.

Figure 11:
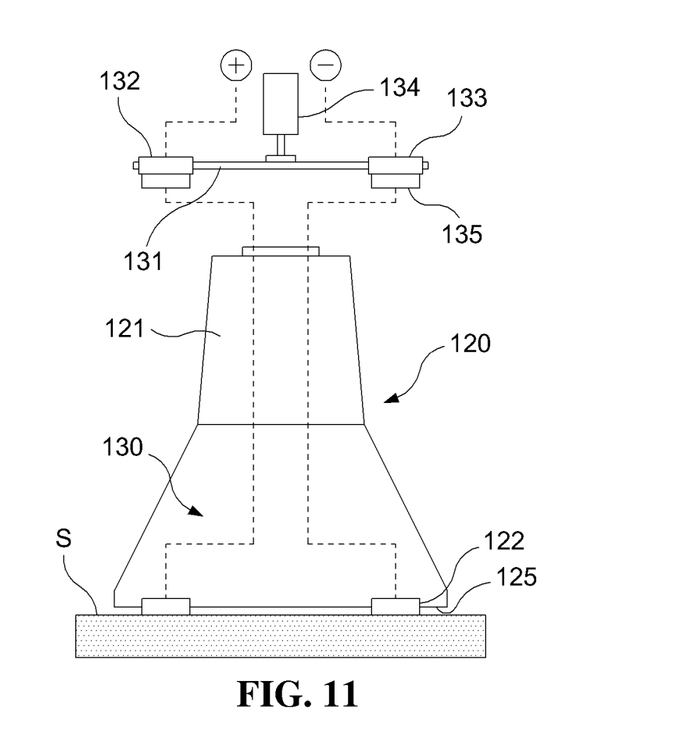
FIG. 11 is a side view illustrating a structure in which an alternating switch is installed in a main body according to the exemplary embodiment of the present invention.

As illustrated in FIG. 11, in a case in which the alternating switch 130 is installed outside the hand piece 120, that is, installed in the main body 110, the alternating switch 130 may include auxiliary electrodes 135 of which the number corresponds to the contact electrodes 122, and which are respectively connected to the contact electrodes 122 through the cable 140 and disposed to be spaced apart from each other by a predetermined distance along a circumference around a center C2 of the alternating switch 130, a rotation plate 131 disposed close to the auxiliary electrodes 135 in the main body 110 to be rotatable about the center C2, a positive pole electrode 132 which is connected to the high frequency generator 114 in a circuit manner, receives a high frequency current with a positive pole, is disposed at one side of the rotation plate 131, and comes into contact with one contact electrode 122 included in any one pair to apply the high frequency current with the positive pole to the one contact electrode 122, a negative pole electrode 133 which is connected to the high frequency generator 114 in a circuit manner, receives a high frequency current with a negative pole, is disposed at the other side of the rotation plate 131, and comes into contact with the other contact electrode 122 included in the pair to apply the high frequency current with the negative pole to the other contact electrode 122, and a drive motor 134 which provides drive power required to rotate the rotation plate 131 and rotates the rotation plate 131 such that the positive pole electrode 132 and the negative pole electrode 133 each sequentially come into contact with the contact electrodes 122. Accordingly, since the hand piece 120 may be miniaturized and lightened when compared to the case in which the alternating switch 130 is installed in the hand piece 120, manipulation fatigue of a hand of an operator can be reduced and operation efficiency can be improved.

Figure 12:
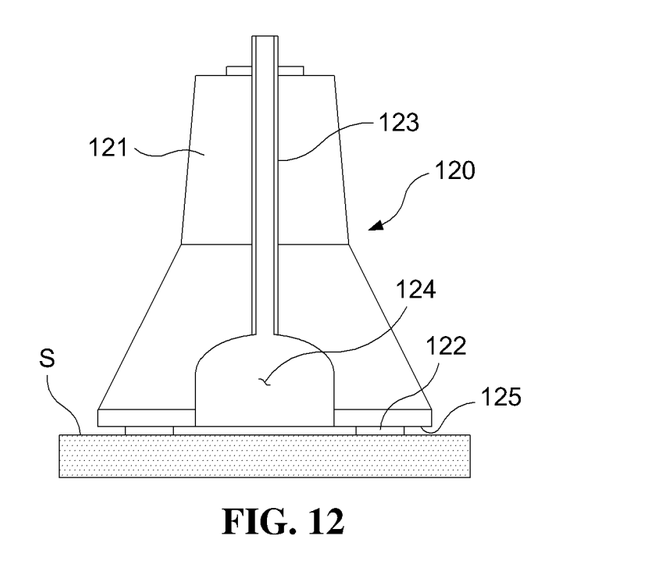
FIGS. 12 to 14 are side views for describing a suction function according to the exemplary embodiment of the present invention.
Figure 13:
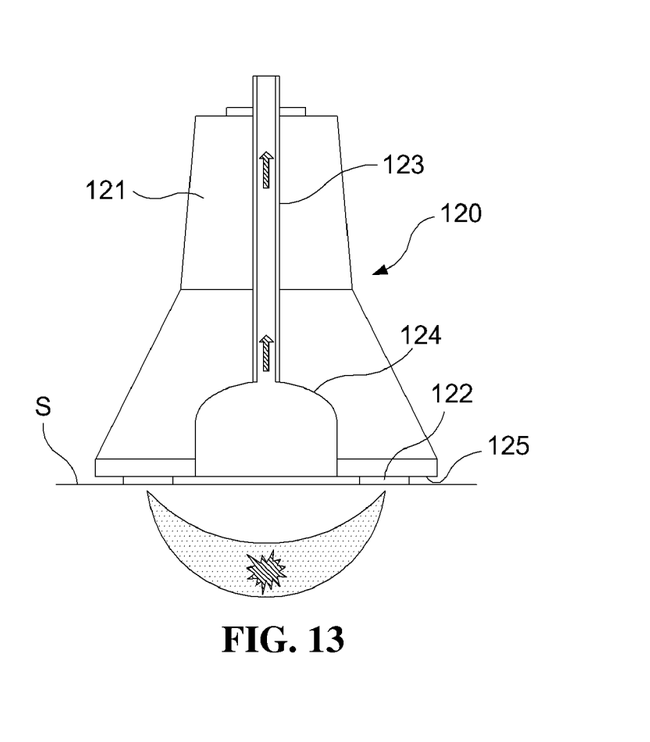
Figure 14:
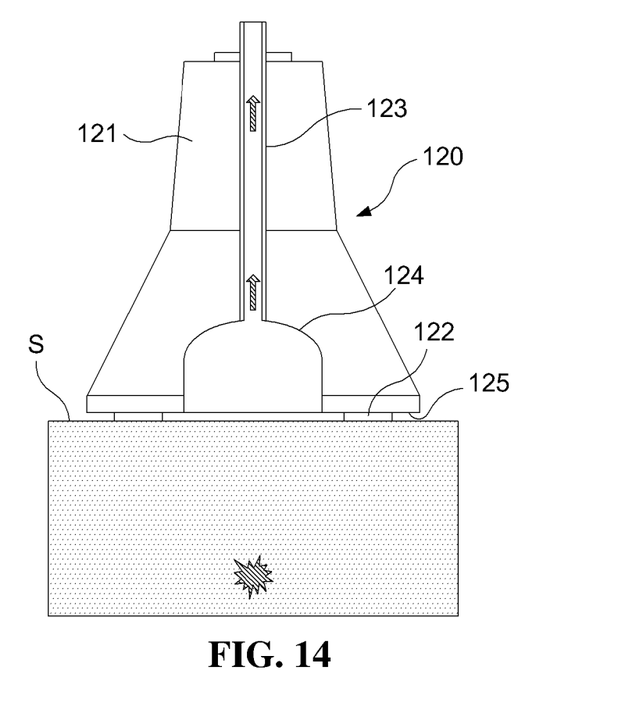
Figure 15:
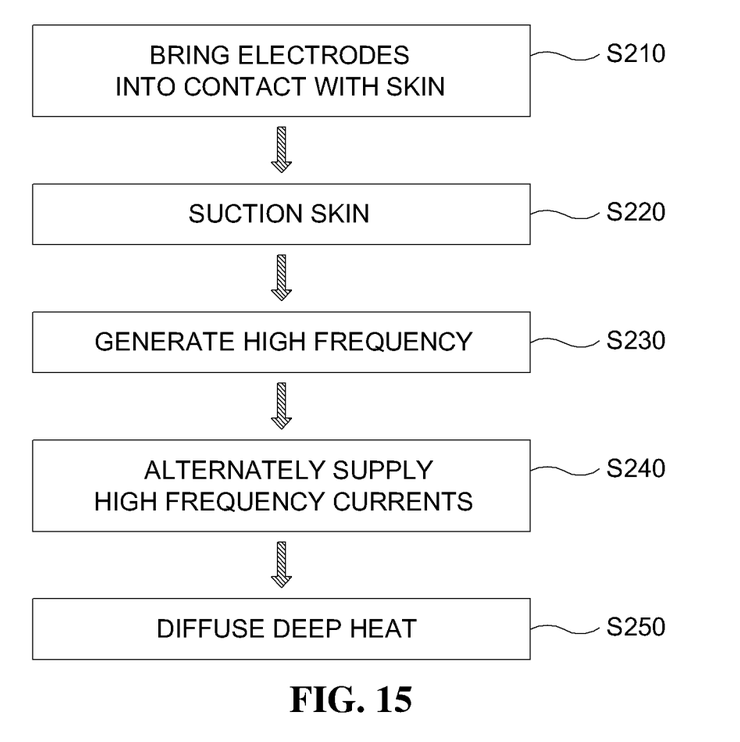
FIG. 15 is a block diagram illustrating an order of a hyperthermia method according to the exemplary embodiment of the present invention.

As illustrated in FIGS. 12 to 14, the main body 110 further includes a suction driver 116 for providing a suction pressure, a suction pipe 123 communicating with a suction end of the suction driver 116 through the cable 140 is disposed in the hand piece 120, and a suction groove 124 which has a shape concavely recessed upward and of which one side communicates with the suction pipe 123 such that the skin S in contact with the lower surface of the hand piece 120 is suctioned therein is formed at a center of the lower surface of the hand piece 120. Therefore, a depth at which deep heat is generated can be deepened downward further when compared to a state in which suction is not performed, and thus a body part at which an operation can be performed can be significantly widened.

According to the above-described structure and function of the high frequency hyperthermia device 100 according to the exemplary embodiment of the present invention, the main body 110 includes the high frequency generator 114 which generates high frequency currents using supplied drive power, the handle 121 to be gripped by the user is provided on the upper portion of the hand piece 120 connected to the main body 110 through the cable 140, four or more contact electrodes 122 which generate deep heat in the internal body by applying the high frequency currents to the contacted skin S and are spaced apart from each other are disposed on the lower surface of the hand piece 120, and the alternating switch 130 which is disposed between and connected to the high frequency generator 114 and the contact electrodes 122 in a circuit manner and supplies the high frequency currents output from the high frequency generator 114 to the contact electrodes 122 alternately supplies the high frequency currents to the pairs, wherein the contact electrodes 122 are divided into the pairs of contact electrodes 122 and the pair includes two contact electrodes 122 so that deep heat can be generated in a short time, a relatively large area can be simultaneously heated to significantly reduce a procedure time and improve a treatment effect, and discomfort, fear, and a burning possibility due to a spark can be minimized by reducing a need to move the contact electrodes 122 in contact with the skin.

According to the high frequency hyperthermia device 100 according to the exemplary embodiment of the present invention, the high frequency hyperthermia device may further comprise one or more LED modules such as diode laser(s) or LED(s) which are disposed on the lower surface of the hand piece (120) and from which light treatment is applied to skin (S). The light may have the specified light wavelength good for the particular skin problems or to kill germs on the skin within safety limits.

In addition, the frequency of the high frequency generator (114) is controlled to change the depth at which deep heat is generated. As the frequency gets higher, the depth at which deep heat gets shallower. As the frequency gets lower, the depth at which deep heat gets deeper.

In addition, the first speed of the alternating switch (130) is controlled to change the amplitude of deep heat. For example, the first speed is preferable to be angular speed or rotational speed faster than 5 rotations per second (5*360 degrees/sec). And the first speed is more preferable to be angular speed or rotational speed faster than 10 rotations per second (10*360 degrees/sec). As the first speed of the alternating switch (130) gets faster, the more deep heat is generated. The more deep heat means that the possibility for patients to feel the deep heat can increase. The first speed may be between a second speed and a third speed faster than the second speed set by the (circuit) designers or automatic algorithms of the high frequency hyperthermia device 100 using treatment data. the first speed may be adjusted or controlled between the second speed and the third speed by the feedback from the patients or people to be treated and feel the deep heat or by sensing the deep heat or temperature on the skin.

In addition, the high frequency currents output from the high frequency generator (114) is controlled to change the amplitude of deep heat. As the high frequency currents applied gets more, deep heat generated gets more.

Next, a hyperthermia method according to the exemplary embodiment of the present invention will be described. As illustrated in FIG. 10, the hyperthermia method according to the exemplary embodiment of the present invention includes bringing electrodes into contact with skin (S210), generating high frequency (S230), and alternately supplying high frequency currents (S240).

In the bringing of the electrode into contact with the skin (S210), the handle 121 of the hand piece 120 is gripped and the contact electrodes 122 simultaneously come into contact with the skin S of a diseased area, and in the generating of the high frequency (S230), the high frequency generator 114 generates high frequency currents according to manipulation of the user input unit 111 of the main body 110.

In the alternately supplying of the high frequency currents (S240), the alternating switch 130 operates to supply the high frequency currents output from the high frequency generator 114 to the contact electrodes 122 such that the high frequency currents are each alternately supplied to the pairs at the first speed to generate deep heat in the skin S in contact therewith.

In this case, after the bringing of the electrode into contact with the skin (S210), suctioning the skin (S220) may be further performed so that the suction driver 116 generates a set suction pressure and suctions the skin S in contact with the hand piece 120 into the suction groove 124.

In addition, after the suctioning of the skin (S220), the alternately supplying of the high frequency currents (S240) may be performed to generate deep heat in a region positioned below the skin S suctioned into the suction groove 124, and after the alternately supplying of the high frequency currents (S240), diffusing the deep heat (S250) for waiting for a predetermined time may be further performed such that the suction driver 116 stops the generating of the suction pressure to return the skin S suctioned into the suction groove 124 to an original position due to elasticity, the region at which the deep heat is generated is returned to an original position, and the deep heat is diffused therearound.

According to the high frequency hyperthermia device and the hyperthermia method using the same according to the present invention, the following effects can be obtained.

First, the main body 110 includes the high frequency generator 114 which generates high frequency currents using supplied drive power, the handle 121 to be gripped by the user is provided at an upper portion of the hand piece 120 connected to the main body 110 through the cable 140, four or more contact electrodes 122, which generate deep heat in the internal body by applying the high frequency currents to the contacted skin S and are spaced apart from each other, are disposed on the lower surface of the hand piece 120, and the alternating switch 130 which is disposed between and connected to the high frequency generator 114 and the contact electrodes 122 in a circuit manner and supplies the high frequency currents output from the high frequency generator 114 to the contact electrodes 122 alternately supplies the high frequency currents to the pairs, wherein the contact electrodes 122 are divided into the pairs of contact electrodes 122 and the pair includes two contact electrodes 122 so that deep heat can be generated in a short time, a relatively large area can be simultaneously heated to significantly reduce a procedure time and improve a treatment effect, and discomfort, fear, and a burning possibility due to a spark can be minimized by reducing a need to move the contact electrodes 122 in contact with the skin.

Second, the contact electrodes 122 are disposed on the lower portion 125 of the hand piece 120 to be spaced apart from each other by a predetermined distance along the circumference around the center C1 of the hand piece 120, the contact electrodes 122 are divided such that two contact electrodes 122 opposite to each other with respect to the center C1 form the pair, and the alternating switch 130 applies a high frequency current with a positive pole to the contact electrode 122 included in the pair and applies a high frequency current with a negative pole to another contact electrode 122, and alternately supplies high frequency currents to the pairs to generate deep heat so that flows of the high frequency currents flowing in the internal body through the pairs of contact electrodes 122 can be concentrated on the central portion, a deep heat generation time can be reduced, and the heat performance can be significantly improved.

Third, the alternating switch 130 is disposed in the hand piece 120 and has the simple structure including the rotation plate 131 disposed close to the contact electrodes 122 in the hand piece 120 to be rotatable about the center C1, the positive pole electrode 132 which is connected to the high frequency generator 114 in a circuit manner, receives a high frequency current with a positive pole, is disposed at one side of the rotation plate 131, and comes into contact with one contact electrode 122 included in any one pair to apply the high frequency current with the positive pole to the one contact electrode 122, the negative pole electrode 133 which is connected to the high frequency generator 114 in a circuit manner, receives a high frequency current with a negative pole, is disposed at the other side of the rotation plate 131, and comes into contact with the other contact electrode 122 of the pair to apply the high frequency current with the negative pole to the other contact electrode 122, and the drive motor 134 which provides drive power required to rotate the rotation plate 131 and rotates the rotation plate 131 so that the positive pole electrode 132 and the negative pole electrode 133 sequentially and alternately come into contact with the contact electrodes 122. Accordingly, the high frequency currents can be alternately applied, and a manufacturing cost and a maintenance cost can be reduced.

Fourth, the alternating switch 130 is disposed in the main body 110 and includes the auxiliary electrodes 135 of which the number corresponds to the contact electrodes 122 and which are respectively connected to the contact electrodes 122 through the cable 140 and disposed to be spaced apart from each other by the predetermined intervals along the circumference thereof around the center C2, the rotation plate 131 disposed close to the auxiliary electrodes 135 in the main body 110 to be rotatable about the center C2, a positive pole electrode 132 which is connected to the high frequency generator 114 in a circuit manner, receives a high frequency current with a positive pole, is disposed at one side of the rotation plate 131, and comes into contact with one contact electrode 122 included in any one pair to apply the high frequency current with the positive pole to the one contact electrode 122, a negative pole electrode 133 which is connected to the high frequency generator 114 in a circuit manner, receives a high frequency current with a negative pole, is disposed at the other side of the rotation plate 131, and comes into contact with the other contact electrode 122 included in the pair to apply the high frequency current with the negative pole to the other contact electrode 122, and a drive motor 134 which provides drive power required to rotate the rotation plate 131 and rotates the rotation plate 131 such that the positive pole electrode 132 and the negative pole electrode 133 each sequentially come into contact with the contact electrodes 122. Accordingly, since the hand piece 120 can be miniaturized and lightened, manipulation fatigue of the hand of the operator can be reduced and operation efficiency can be improved.

Fifth, the main body 110 further includes the suction driver 116 for providing a suction pressure, the suction pipe 123 communicating with the suction end of the suction driver 116 through the cable 140 is disposed in the hand piece 120, and the suction groove 124 which has the shape concavely recessed upward and of which one side communicates with the suction pipe 123 such that the skin S in contact with the lower portion 125 of the hand piece 120 is suctioned therein and is formed at the center of the lower portion 125 of the hand piece 120. Therefore, a depth at which deep heat is generated can be deepened downward, and thus a body part on which an operation can be performed can be significantly increased.

As described above, although the present disclosure has been shown and described with reference to the few specific embodiments and drawings, those skilled in the art should appreciate that various modifications and changes may be made in the technical concept of the present disclosure, the scope of which is defined in the claims and their equivalents.

What is claimed is:

1. A high frequency hyperthermia device comprising:
    a main body including a high frequency generator which generates high frequency currents using drive power;
    a hand piece which is connected to the main body through a cable and in which a handle to be gripped by a user is disposed on an upper portion of the hand piece and four or more contact electrodes, through which the high frequency currents being supplied are applied to skin in contact with the contact electrodes to generate deep heat in an internal body, are disposed on a lower surface of the hand piece; and
    an alternating switch which is disposed between and connected to the high frequency generator and the contact electrodes in a circuit manner and which supplies the high frequency currents output from the high frequency generator to the contact electrode, wherein the contact electrodes are divided into pairs each having two contact electrodes, and the high frequency currents are alternately supplied to the pairs at a first speed,
    wherein the contact electrodes are disposed on a lower portion of the hand piece to be spaced apart from each other by a predetermined distance along a circumference around a center of the hand piece,
    wherein the alternating switch applies the high frequency current with a positive pole to one contact electrode and the high frequency current with a negative pole to the other contact electrode to alternately supply the high frequency currents to each of the pairs so as to generate the deep heat, wherein the contact electrodes are divided into the pairs such that two contact electrodes opposite to each other with respect to the center of the hand piece form the pair,
    wherein flows of the high frequency currents flowing in the internal body are concentrated on a central portion by the pairs of the contact electrodes to decrease a deep heat generation time and significantly improve heat performance,
    wherein the alternating switch, which is disposed in the hand piece, includes:
    a rotation plate disposed close to the contact electrodes in the hand piece to be rotatable about the center of the hand piece;
    a positive pole electrode which is connected to the high frequency generator in a circuit manner, receives the high frequency current with the positive pole, is disposed at one side of the rotation plate, and comes into contact with one contact electrode included in any one pair to apply the high frequency current with the positive pole to the one contact electrode;
    a negative pole electrode which is connected to the high frequency generator in a circuit manner, receives the high frequency current with the negative pole, is disposed at the other side of the rotation plate, and comes into contact with the other contact electrode of the pair to apply the high frequency current with the negative pole to the other contact electrode; and
    a drive motor which provides drive power required to rotate the rotation plate and rotates the rotation plate so that the positive pole electrode and the negative pole electrode sequentially and alternately come into contact with the contact electrodes, and
    wherein sizes of the positive pole electrode and the negative pole electrode are relatively greater than distances between the contact electrodes installed on the lower portion of the hand piece to simultaneously come into contact with two adjacent contact electrodes.

2. The high frequency hyperthermia device of claim 1, wherein the alternating switch, which is disposed in the main body, includes:
    auxiliary electrodes of which the number corresponds to the contact electrodes and which are respectively connected to the contact electrodes through the cable and disposed to be spaced apart from each other by a predetermined distance along a circumference around a center of the alternating switch;
    a rotation plate disposed close to the auxiliary electrodes in the main body to be rotatable about the center of the alternating switch;
    a positive pole electrode which is connected to the high frequency generator in a circuit manner, receives the high frequency current with the positive pole, is disposed at one side of the rotation plate, and comes into contact with one contact electrode included in any one pair to apply the high frequency current with the positive pole to the one contact electrode;
    a negative pole electrode which is connected to the high frequency generator in a circuit manner, receives the high frequency current with the negative pole, is disposed at the other side of the rotation plate, and comes into contact with the other contact electrode included in the pair to apply the high frequency current with the negative pole to the other contact electrode; and
    a drive motor which provides drive power required to rotate the rotation plate and rotates the rotation plate such that the positive pole electrode and the negative pole electrode each sequentially come into contact with the contact electrodes.

3. The high frequency hyperthermia device of claim 1, wherein:
    the main body further includes a suction driver which provides a suction pressure;
    a suction pipe communicating with a suction end of the suction driver through the cable is disposed in the hand piece; and
    a suction groove, which has a shape concavely recessed upward and of which one side communicates with the suction pipe such that the skin in contact with the lower portion of the hand piece is suctioned into the suction groove, is formed at a center of the lower portion of the hand piece.

4. The high frequency hyperthermia device of claim 1, further comprising one or more LED modules which are disposed on the lower surface of the hand piece and from which light treatment is applied to the skin.

5. The high frequency hyperthermia device of claim 2, further comprising one or more LED modules which are disposed on the lower surface of the hand piece and from which light treatment is applied to the skin.

6. The high frequency hyperthermia device of claim 3, further comprising one or more LED modules which are disposed on the lower surface of the hand piece and from which light treatment is applied to the skin.

7. The high frequency hyperthermia device of claim 1, wherein the frequency of the high frequency generator is controlled to change the depth at which deep heat is generated.

8. The high frequency hyperthermia device of claim 2, wherein the frequency of the high frequency generator is controlled to change the depth at which deep heat is generated.

9. The high frequency hyperthermia device of claim 3, wherein the frequency of the high frequency generator is controlled to change the depth at which deep heat is generated.

10. The high frequency hyperthermia device of claim 1, wherein the first speed of the alternating switch or the high frequency currents output from the high frequency generator is controlled to change the amplitude of deep heat.

11. The high frequency hyperthermia device of claim 2, wherein the first speed of the alternating switch or the high frequency currents output from the high frequency generator is controlled to change the amplitude of deep heat.

12. The high frequency hyperthermia device of claim 3, wherein the first speed of the alternating switch or the high frequency currents output from the high frequency generator is controlled to change the amplitude of deep heat.

* * * * *